(12) United States Patent
Sinha et al.

(10) Patent No.: US 7,741,508 B2
(45) Date of Patent: Jun. 22, 2010

(54) **SINGLE STEP GREEN PROCESS FOR THE PREPARATION OF SUBSTITUTED CINNAMIC ESTERS WITH *TRANS*-SELECTIVITY**

(75) Inventors: Arun Kumar Sinha, Himachal Pradesh (IN); Anuj Sharma, Himachal Pradesh (IN); Anand Swaroop, Himachal Pradesh (IN); Vinod Kumar, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 11/728,721

(22) Filed: Mar. 26, 2007

(65) Prior Publication Data

US 2008/0045742 A1 Feb. 21, 2008

(30) Foreign Application Priority Data

Mar. 30, 2006 (IN) ............................ 892/DEL/2006

(51) Int. Cl.
*C07C 69/76* (2006.01)
(52) U.S. Cl. .................... 560/55; 560/103; 560/104; 560/128; 526/318.1
(58) Field of Classification Search ................. 560/104, 560/103, 55, 128; 526/318.1
See application file for complete search history.

(56) References Cited

U.S. PATENT DOCUMENTS

| | | | | |
|---|---|---|---|---|
| 4,132,726 A * | 1/1979 | Kurozumi et al. | ........... | 549/421 |
| 6,054,607 A | 4/2000 | Okui et al. | ................... | 560/210 |
| 6,531,625 B2 * | 3/2003 | Kuhn et al. | ................. | 560/104 |
| 6,538,154 B2 * | 3/2003 | Kuhn et al. | ................. | 560/104 |
| 6,566,557 B2 * | 5/2003 | Sinha et al. | ................ | 568/431 |
| 6,927,302 B2 * | 8/2005 | Eckert et al. | ................ | 560/104 |

OTHER PUBLICATIONS

Rhee et al. Tetrahedron Letters 39 (1998) 1365-1368.*
Sinha et al. Tetrahedron 63 (2007) 1000-1007.*
Xiang et al. Angew. Chem. Int. Ed. 2001, 40. No. 19 pp. 3670-3672.*
Wilson et al. JOrgCh (1982), 47(7), 1360-1.*

(Continued)

*Primary Examiner*—Porfirio Nazario Gonzalez
*Assistant Examiner*—Yate' K Cutliff
(74) *Attorney, Agent, or Firm*—DLA Piper LLP (US)

(57) ABSTRACT

The invention provides a green process for direct oxidation of a large number of substituted or unsubstituted cinnamaldehydes or cinnamyl alcohols into the corresponding alkyl or aryl cinnamates in one step. The process of the present invention is a convenient and efficient green process for the preparation of various aryl or alkyl cinnamates under conventional, microwave and ultrasound directly from cinnamaldehydes or cinnamyl alcohols in the presence of an oxidizing agent, catalyst and an alcohol, with or without an organic solvent. These esters are immensely important compounds in flavor, perfumery and pharmaceutical industries. There are several prior arts available for the preparation of cinnamic esters, but all of them suffer from deficiencies such as use of expensive reagents and catalysts, harsh reaction conditions, use of toxic chemicals and others. In contrast, the present methodology is extremely simple and involves reaction of the substrate with an oxidizing agent mixed with a homogeneous or heterogeneous catalyst and an alcohol with or without organic solvent by stirring at room temperature or refluxing or under microwave or ultrasound irradiation to get the requisite products.

34 Claims, 4 Drawing Sheets

OTHER PUBLICATIONS

Foot et al. Synthesis 2003 No. 7 1055-1064.*
Foot et al. SynLett 2002 No. 8 1293-1295.*
Sinha et al. Indian JourChem (2002) 41B (3) 635-638.*
Foot et al., "Esters and Amides from Activated Alcohols using Manganese(IV) Dioxide: Tandem Oxidation Processes," *Synthesis* 2003, 7:1055-1064.
Foot et al., "Tandem Oxidation Processes, the Direct Conversion of Activated Alcohols into Esters and Amides," *Synlett*, 2002, 8:1293-1295.
Rhee and Kim, "A Simple One-Pot Procedure for the Conversion of Aldehydes to Methyl Esters," *Tetrahedron Letters*, 1998, 39:1365-1368.
Sinha et al., "A concise conversion of β-asarone into 1-(3'-methoxypropanoyl)-2, 4, 5-trimethoxybenzene occurring *Cordia alliodora*," *Indian Journal of Chemistry* 2002, 41B:635-638.
Xiang et al., "A Practical and Green Chemical Process: Fluoroalkyldistannoxane-Catalyzed Biphasic Transesterification," *Angew. Chem. Int. Ed.*, 2001, 40(19): 3670-3672.

* cited by examiner

SINGLE STEP GREEN PROCESS FOR THE PREPARATION OF SUBSTITUTED CINNAMIC ESTERS WITH *TRANS*-SELECTIVITY

CROSS REFERENCE TO RELATED APPLICATION

This application is a utility application and claims the benefit under 35 USC §119(a) of India Application No. 892/DEL/2006 filed Mar. 30, 2006. This disclosure of the prior application is considered part of and is incorporated by reference in the disclosure of this application.

BACKGROUND OF THE INVENTION

1. Field of the Invention

The present invention relates to a single step Green Process for the Preparation of Substituted Cinnamic Esters with trans-Selectivity. The present invention particularly relates to a process of conversion of cinnamyl alcohol or cinnamaldehyde to corresponding esters directly. Cinnamic esters are commercially important products in cosmetics, lubricants, plasticizers and perfumes.

2. Background Information

Cinnamic esters are immensely important organic compounds due to their applications in a wide range of products such as cosmetics, lubricants, plasticizers and perfumes (A. Steffen, *Perfume and Flavor Chemicals (Aroma Chemicals)*, Vol. I & II. Allured Publishing Corporation: IL, USA, 1994). These esters are useful as a material for perfumes, as cinnamic aldehydes, and for the synthesis of β-amyl cinnamic aldehydes and the like. These esters can themselves be used as precursors for the synthesis of polyhetroalkylene esters which can be useful as raw materials for the synthesis of perfumes, drugs and as organic synthetic intermediates and as polymerisable materials and so forth (K. Yurugi, T. Kubo, U.S. Pat. No. 6,541,656, 2003).

A number of prior arts are available for the synthesis of cinnamic esters (A. Galat, *J. Am. Chem. Soc.*, 1946, 68, 376; V. T. Ramakrishnan, J. Kagan, *J. Org. Chem.*, 1970, 35, 2901; H. Tanaka, S. Takamuku, H. Sakurai, *Bull. Chem. Soc. Jpn.*, 1979, 52, 801; Y. Oikaw, T. Yoshioka, O. Yonemitsu, *Tetrahedron Lett.*, 1982, 23, 889; U. Tataki, I. Suso, T. Matsuhisa, I. Hara, U.S. Pat. No. 4,661,620, 1987; B. Gerhard, K. Jochen, S. Werner, U.S. Pat. No. 5,124,478, 1992; Z. Wang, F. R. W. McCourt, D. A. Holden, *Macromolecules*, 1992, 25, 1576; T. Iliefski, S. Li, K. Lundquist, *Tetrahedron Lett.*, 1998, 39, 2413; V. L. Pardini, S. K. Sakata, R. R. Vargas, H. Viertler, *J. Braz. Chem. Soc.*, 2001, 12, 223; H. Weissman, X. Song, D. Milstein, *J. Am. Chem. Soc.*, 2001, 123, 337; K. M. Bushan, G. V. Rao, T. Soujanya, V. J. Rao, S. Saha, A. Samanta, *J. Org. Chem.*, 2001, 66, 681; A. Stadler, C. O. Kappe, *Tetrahedron*, 2001, 57, 3915; P. Kisnaga, B. Dsa, J. Verkade, *Tetrahedron*, 2001, 57, 8047; B. Deevi, J. R. Anumolu, *Synth. Commun.*, 2002, 32, 195; C. S. Cho, D. T. Kim, H. J. Choi, T. J. Kim, S. C. Shim, *Bull. Korean Chem. Soc.*, 2002, 23, 539; R. Borah, D. J. Kalita, J. C. Sarma, *Ind. J. Chem.*, 2002, 41B, 1032; S. F. Jonathan, K. Hisashi, M. P. G. Gerard, J. K. T. Richard, *Synlett*, 2002, 8, 1293; S. Crosignani, P. D. White, B. Linclau, *Org. Lett.*, 2002, 4, 2961; O. Uchikawa, K. Fukatsu, R. Tokunoh, M. Kawada, K. Matsumoto, Y. Imai, S. Hinuma, K. Kato, H. Nishikawa, K. Hirai, M. Miyamoto, S. Ohkawa, *J. Med. Chem.*, 2002, 45, 4222; A. Costa, C. Nájera, J. M. Sansano, *J. Org Chem.*, 2002, 67, 5216; W. C. Shieh, S. Dell, O. Repic, *Tetrahedron Lett.*, 2002, 43, 5607; A. Palma, B. A. Frontana-Uribe, J. Cardenas, M. Saloma, *Electrochem. Commun.*, 2003, 5, 455; S. Crosignani, P. D. White, R. Steinauer, B. Linclau, *Org. Lett.*, 2003, 5, 853; H. M. S. Kumar, M. S. Kumar, S. Joyasawal, J. S. Yadav, *Tetrahedron Lett.*, 2003, 44, 4287; N. N. Karade, S. G. Shirodkar, R. A. Potrekar, *Synth. Commun.*, 2004, 34, 391; R. B. Andrew, C. G. IV Louis, *Synlett*, 2004, 738; T. J. Speed, J. P. McIntyre, D. M. Thamattoor, *J. Chem. Edu.* 2004, 81, 1355; D. Penningt, M. A. Russell, B. B. Chen, H. Y. Chen, B. N. Desai, S. H. Docter, D. J. Edwards, G. J. Gesicki, C. D. Liang, J. W. Malecha, S. S. Yu, V. W. Engleman, S. K. Freeman, M. L. Hanneke, K. E. Shannon, M. M. Westlin, G. A. Nickels, *Bioorg. Med. Chem. Lett.*, 2004, 14, 1471; J. M. Concellon, H. R. Solla, C. Mejica, *Tetrahedron Lett.*, 2004, 45, 2977; D. K. Barma, A. Kundu, A. Bandyopadhyay, A. Kundu, B. Sangras, A. Briot, C. Mioskowski, J. R. Falck, *Tetrahedron Lett.*, 2004, 45, 5917; R. Ballini, D. Fiorini, A. Palmieri, *Tetrahedron Lett.*, 2004, 45, 7027; G. Deng, B. Xu, C. Liu, *Tetrahedron*, 2005, 61, 5818). The most common being acid catalysed esterification of the cinnamic acids in the presence of appropriate alcohols ((a) I. A. Pearl, D. L. Beyer, *J. Org. Chem.*, 1951, 16, 216; (b) L. H. Klemm, R. A. Klemm, P. S. Santhanam, D. V. White, *J. Org. Chem.*, 1971, 36, 2169; (c) B. Botta, G. D. Monache, M. C. De Rosa, A. Carbonetti, E. Gacs-Baitz, M. Botta, F. Corelli, D. Misiti, *J. Org. Chem.*, 1995, 60, 3657; (d) A. Ewenson, B. Croitoru, A. Shushan, U.S. Pat. No. 728,865, 1998; (e) A. M. S. Silva, I. Alkorta, J. Elguero, V. L. M. Silva, *J. Mol. Struct.*, 2001, 595), however, the reaction is reversible and the acids employed may not be compatible with many sensitive functional groups attached at either the aromatic ring or the alkyl chains such as alkoxy, halogens and the like.

Similarly, Org. Synth. Coll. Vol. 1, 252, discloses a method for the preparation of ethyl cinnamate by reaction of benzaldehyde, ethylacetate and ethanol and sodium as dispersed pieces. However, the process suffers from the use of highly inflammable sodium. Another conventional approach for the synthesis of cinnamates is the Claisen condensation between benzaldehydes and acetic acid esters (A. I. Vogel, A Textbook of Practical Organic Chemistry, Richard Clay (The Chaucer Press), Ltd., Bungay, Suffolk, 1978) in the presence of a strong base such as sodium salts of acetic acids and again the method has limitation for a number of substituted benzaldehydes. Moreover, the reactions are reported to take invariably long time for completion which adds to the mundane of the chemists and unnecessarily utilize energy resources in industries.

Heck came up with a different route for the synthesis of α,β-unsaturated acids (Heck. et al., *J. Amer. Chem. Soc.*, 1969, 6707) by reaction between aryl halides and aryl acrylate using palladium acetate and a base as catalyst. Although, the method provided good yield of the product, it still suffers from expensive reagents used in the reaction.

Another modification of Heck reaction came in the form of Stille reaction (Stille et al., *J. Amer. Chem. Soc.*, 1976, 1806) wherein alkyl boronic acids are being taken as the substrates and are reacted with aryl halides. However, the reaction also requires presence of copper salts (II) in stoichiometric amounts as oxidants in these reactions.

The following prior art references are disclosed:

Commetti and Chiusoli (*J. Organometal. Chem.*, 1979, 181, C14) discloses a method for synthesis of methyl cinnamate by reaction of styrene, carbon monoxide and methanol in the presence of palladium as catalyst, but again it has a shortfall in terms of use of excess Cu (II) salt as oxidant which renders the process industrially unviable.

Similarly, many patents disclose the method for the preparation of cinnamic esters as discussed below:

J.P. Pat. No. 21342 discloses a method for the production of methyl cinnamate through oxidative carbonylation of styrenes wherein it was further disclosed that use of an excess dehydrating agent may cause increase in the yield the product and good yields could be obtained. However, use of excess dehydrating agent was an impediment in this transformation.

J.P. Pat. No. 21343 discloses a method for the production of methyl cinnamates by reacting styrenes, aliphatic alcohols, carbon monoxide and palladium but again the method has its drawback in the form of using expensive dehydrating agent.

U.S. Pat. No. 4,737,591, 1988 discloses a method for the cinnamate derivatives by reacting styrenes, aliphatic alcohols, carbon monoxide, palladium chloride and copper salt without any dehydrating agent, but poor yield of the product was obtained.

D.E. Pat. No. 7,099,227 discloses a method for the preparation of ethyl cinnamate by condensing benzaldehyde and ethyl acetate in the presence of sodium hydride as a base. Sodium hydride, however, is not easy to handle and is expensive and so the process demands improvement.

U.S. Pat. No. 4,618,698, 1986 discloses a method for the preparation of optionally substituted cinnamic acid by treatment of optionally substituted benzaldehyde and acetic acid ester and alcohol to form an optionally substituted cinnamic acid ester as well as alkoxy phenyl propionic acid which then was hydrolyzed into optionally substituted cinnamic acid. This was finally esterified to provide the cinnamic ester. The reaction suffers from tedius of multi step synthesis and demands rectification.

U.S. Pat. No. 6,054,607, 2000 discloses a method for the preparation of cinnamic acid esters by condensing a benzaldehyde with an acetic acid ester in the presence of a base followed by treatment with an acid to form alkoxy phenyl-propionic acid ester which is then treated with an acid to provide the cinnamic ester. In addition, many patents (U.S. Pat. Nos. 3,381,030, 3,397,225, 3,397,226, 3,530,168, 3,621,054) also discloses the method for the preparation of cinnamic esters. Though, the many above mentioned methods provide good yield of the product, the reaction conditions are not mild and resort to ultra low temperature there by making it difficult to control the reaction.

In 1968, Corey, Gilman and Ganem presented a unique approach of converting α,β-unsaturated aldehydes directly into their methyl esters using manganese dioxide, sodium cyanide and acetic acid in methanol (E. J. Corey, N. W. Gilman, B. E. Ganem, *J. Am. Chem. Soc.,* 1968, 90, 5616). This revolutionary method made a remarkable impact in organic chemistry and has been instrumental in the synthesis of various complex natural products (E. J. Corey, J. A. Katzenenllenbogen, N. W. Gilmen, S. A. Romen, B. W. Erickson, *J. Am. Chem. Soc.,* 1968, 90, 5618; A. D. Adams, R. H. Schlessinger, J. R. Tata, J. J. Venit, *J. Org. Chem.,* 1986, 51, 3070).

The above method continued to attract the attention of researchers for direct conversion of aldehydes or alcohols into esters and various prior arts are available for this conversion using a range of reagents such as $MnO_2$—NaCN (A. B. III Smith, G. A. Sulikowski, M. M. Sulikowski, K. Fujimoto, *J. Amer. Chem. Soc.,* 1992, 114, 2567; J. S. Foot, H. Kanno, G. M. P. Giblin, R. J. K. Taylor, *Synlett,* 2002, 1393), chromium oxide-pyridine (E. J. Corey, B. Samuelsson, *J. Org. Chem.,* 1984, 49, 4735), t-butyl hypochlorite (J. N. Milovanovic, M. Vasojevic, S. Gojkovic, *J. Chem. Soc. Perkin Trans 2,* 1991, 1231) and PhIO—KBr (H. Tohma, T. Maegawa, Y. Kita, *Synlett,* 2003, 723) etc. There are other prior arts such as *Tetrahedron Lett.,* 1982, 23, 4647; *Tetrahedron,* 1982, 38, 337; *J. Org. Chem.,* 1968, 33, 2525; *J. Amer. Chem. Soc.,* 1976, 98, 1629 etc for the preparation of esters.

Although methods for direct conversion of cinnamaldehyde ($C_6$-$C_3$ unit) or cinnamyl alcohol ($C_6$-$C_3$ unit) into cinnamic esters ($C_6$-$C_3$ unit) are meritorious but have certain limitations. First, all these methods pass through an intermediate $C_6$-$C_4$ unit, formed by combination of substrate $C_6$-$C_3$ unit and an extra $C_1$ unit in the form of sodium/potassium cyanide or TMSCN (B. S. Bal, W. E. Childers Jr., H. W. Pinnick, *Tetrahedron,* 1981, 37, 2091; A. D. Adams, R. H. Schlessinger, J. R. Tata, J. J. Venit, *J. Org. Chem.,* 1986, 51, 3070) etc. and overall, the protocols confer lack of atom economy. Secondly, use of hazardous cyanide reagents make the process more and more unviable for industrial use. In the contemporary concerns for Green chemistry, there has been a tremendous upsurge of interest in various chemical transformations mediated by Green technologies (T. J. Mason, P. Cintas in *Handbook Of Green Chemistry and Technology* (Eds.: J. Clark, D. Macquarrie), Blackwell Publishing, 2002, pp. 372) such as atom economical processes, reactions in aqueous media, reusable heterogeneous catalysts, use of ultrasound and microwave (B. L. Hayes, *Microwaves Synthesis: Chemistry at the Speed of Light,* CEM Publishing: Matthews N.C., 2002; N. F. K. Kaiser, U. Bremberg, M. Larhed, C. Moberg, A. Hallberg, *Angew. Chem. Int. Ed.,* 2000, 39, 3596; P. Lidstrom, J. Tierney, B. Wathey, J. Westman, *Tetrahedron,* 2001, 57, 9225; M. Larhed, A. Hallberg, *Drug Discov. Today,* 2001, 6, 406; A. K. Bose, M. S. Manhas, S. N. Ganguly, A. H. Sharma, B. K. Banik, *Synthesis,* 2002, 11, 1578; K. J. Watkins, *Chem. Eng. News,* 2002, 80, 17; N. E. Leadbeater, H. M. Torenius, *J. Org. Chem.,* 2002, 67, 3145; L. Botella, C. Nájera, *Tetrahedron Lett.,* 2004, 60, 5563; N. Kaval, W. Dehaen, P. Mátyus, E. V. Eycken, *Green Chem.,* 2004, 6, 125; V. Pathania, A. Sharma, A. K. Sinha, *Helv. Chim. Acta,* 2005, 88, 811; B. P. Joshi, A. Sharma, A. K. Sinha, *Tetrahedron,* 2005, 61, 3075) for organic transformations.

Cinnamic esters are of immense importance in organic chemistry due to synthetic utility ((a) T. Ohno, Y. Ishino, Y. Sumagari, I. Nishiguchi, *J. Org. Chem.,* 1995, 60, 458; (b) B. Botta, G. D. Monache, M. C. De Rosa, A. Carbonetti, E. Gacs-Baitz, M. Botta, F. Corelli, D. Misiti, *J. Org. Chem.,* 1995, 60, 3657; (c) F. Xu, R. D. Tillyer, D. M. Tschaen, E. J. J. Grabowski, P. J. Reider, *Tetrahedron Asymmetry,* 1998, 9, 1651; (d) M. Carmignani, A. R. Volpe, F. D. Monache, B. Botta, R. Espinal, S. C. De Bonnevaux, C. De Luca, M. Botta, F. Corelli, A. Tafi, G. Ripanti, G. D. Monache, *J. Med. Chem.,* 1999, 42, 3116; (e) G. Li, H. X. Wei, S. H. Kim, *Org. Lett.,* 2000, 2, 2249; (f) H. X. Wei, S. H. Kimm, G. Li, *Tetrahedron,* 2001, 57, 3869; (g) G. Li, H. X. Wei, S. H. Kim, *Tetrahedron,* 2001, 57, 8407; (h) R. K. Lamni, A. Ambroise, T. Balasubramanian, R. W. Wagner, D. F. Bocian, D. Holten, J. Lindsey, *J. Amer. Chem. Soc.,* 2002, 122, 7579) of the ensuing cinnamic esters beside their applications in a wide range of products such as cosmetics, lubricants, plasticizers and perfumes (A. Steffen, *Perfume and Flavor Chemicals (Aroma Chemicals),* Vol. I & II. Allured Publishing Corporation: IL, USA, 1994). More importantly, these esters possess a variety of pharmacological activities including antioxidant (J. Chalas, C. Claise, M. Edeas, C. Messaoudi, L. Vergnes, A. Abella, *Biomed. Pharmacother.,* 2001, 55, 54), glycosidase inhibiton (A. Sirichai, S. Kasem, R. Sophon, P. Amom, N. Nattaya, C. Warinthom, D. Sujitra, Y. A. Sirintom, *Bioorg. Med. Chem. Lett.,* 2004, 14, 2893), and steroidogenesis inhibition activities (S. Gobec, M. Sova, K. Kristan, T. L. Rizner, *Bioorg. Med. Chem. Lett.,* 2004, 14, 3933). For example, 17b-hydroxysteroid dehydrogenases (17b-HSDs), involved in the synthesis of active 17b-hydroxy-forms (such as estradiol, testosterone, and dihydrotestosterone) using NAD(P)H or NAD(P) as cofactor, play a key role in hormonal regulation and function in the human and constitute emerging therapeutic targets for the control of estrogeno- and androgeno-sensitive diseases like breast cancer, endometrial cancer, prostate cancer, benign prostatic hyperplasia, acne, hair loss, etc. 17b-HSDs are implicated also in the development of polycystic kidney disease, pseudohermaphroditism, Zellweger syndrome and Alzheimer's disease ((a) J. Adamski, J. F. Jakob, *Mol. Cell. Endocrinol.*, 2001, 171, 1; (b) H. Peltoketo, V. Luu-The, J. Simard, J. Adamski, *J. Mol. Endocrinol.*, 1999, 23, 1). Similarly, $\alpha$-glucosidase inhibitors have been shown to be potentially valuable for treatment of various diseases. These $\alpha$-glucosidase inhibitors are known to be promising as anti-viral, anti-HIV agents, which alter glycosidation of envelope glycoprotein through interference with biosynthesis of N-linked oligosaccharides (P. B. Fischer, G. B. Karlsson, T. D. Butters, R. A. Dwek, F. M. J. Platt, *Virol.*, 1996, 70, 7143; (b) B. D. Walker, M. Kowalski, W. C. Goh, K. Kozarsky, M. Krieger, C. Rosen, L. Rohrschneider, W. A. Haseltine, J. Sodroski, *Proc. Natl. Acad. Sci. USA.*, 1987, 84, 8120). In addition, they have recently been used for treatment of B- and C type viral hepatitis (T. M. Block, X. Y. Lu, F. M. Platt, G. R. Foster, W. H. Gerlich, B. S. Blumberg, R. A. Dwek, *Proc. Natl. Acad. Sci. U.S.A.*, 1994, 91, 2235). A number of cinnamic acids and esters have been reported to be active $\alpha$-glucosidase inhibiting agents (S. Adisakwattana, K. Sookkongwaree, S. Roengsumran, A. Petsom, N. Ngamrojnavanich, W. Chavasiri, S. Deesamerc, S. Y. -Anuna, *Bioorg. Med. Chem. Lett.*, 2004, 14, 2893).

Similarly, the higher esters of substituted cinnamic acids, particularly the octyl methoxy cinnamates, are well known sunscreen agents which possess high absorption in the 300-400 nm range and which are ideally suited for cosmetic applications since they are non-irritating to the skin and provide lubricity to prevent drying effects of wind and sun (A. Alexander, R. K. Chaudhari, U.S. Pat. No. 5,527,947, 1996). Moreover, cinnamic acids and cinnamates are used as a material for perfumes, as cinnamic aldehydes, cyclamen aldehyde, beta-amyl cinnamic aldehyde and the like.

There are a number of methods available for the synthesis of cinnamic esters as being discussed in detail in the prior art section. But all of the reported inventions suffer from expensive reagents, and substrates, low yields, long reaction periods, multi-steps approach, many bye-products, hazardous reagents and chemicals, all of which combinedly call for an improved method for the synthesis of cinnamic esters. In recent years, there has been a tremendous upsurge of interest in various chemical transformations mediated by reusable heterogeneous catalysts due to environmental and economical considerations ((a) P. Laszlo, *Acc. Chem. Res.*, 1986, 19, 121; (b) S. V. Ley, I. R. Baxendale, R. N. Bream, P. S. Jackson, A. G. Leach, D. A. Longbottom, M. Nesi, J. S. Scott, R. J. Storter, S. J. Taylor, *J. Chem. Soc., Perkin Trans. I*, 2000, 3815; (c) R. Fricke, H. Hosslick, G. Lischke, M. Richter, *Chem. Rev.*, 2000, 100, 2303. (d) R. Ballini, G. Bosica, R. Maggi, A. Mazzacani, P. Righi, G. Sartori, *Synthesis*, 2001, 12, 1826). Reactions assisted by heterogeneous catalysis have revolutionized the organic synthesis due to higher yields, easy work up and recyclability of the catalysts.

In our constant endeavor towards synthesis of important bioactive compounds ((a) A. K. Sinha, B. P. Joshi, R. Acharya, *Chem. Lett.*, 2003, 32, 780; (b) A. Sharma, B. P. Joshi, A. K. Sinha, *Bull. Chem. Soc. Jpn.*, 2004, 77, 2231; (c) V. Pathania, A. Sharma, A. K. Sinha, *Helv. Chim. Acta*, 2005, 88, 811), we were interested to develop conversion methodologies for commercially available economical cinnamaldehydes or cinnamyl alcohols into important bioactive cinnamates.

In this context, we, herein, disclose, a convenient and efficient green process for the preparation of various aryl or alkyl cinnamates under conventional, microwave and ultrasound directly from cinnamaldehydes or cinnamyl alcohols in the presence of an oxidizing agent, catalyst and an alcohol, with or without an organic solvent.

OBJECTIVES OF THE INVENTION

The main object of the present invention is to provide a green process for the preparation of substituted cinnamic esters with trans-selectivity.

Another object of the present invention is to develop a convenient and green process for the direct oxidation of cinnamaldehydes or cinnamyl alcohols into cinnamic esters.

Yet another object of the present invention is to develop a process which may be carried out without organic solvents depending upon the alcohol used.

Yet another object of the present invention is to develop a simple process for the preparation of cinnamic esters in high purity with minimum formation of side products.

Yet another object of the present invention is to employ eco-friendly protocols as recyclable reagents, microwave and ultrasound for the preparation of product.

Still another object of the present invention is to develop a green process, in which heterogeneous catalyst used for carrying out the reaction is recyclable and reused for a number of times preferably 5 to 15 times, without any significant loss in the activity.

Yet another object of the present invention is to avoid use of any toxic and hazardous compound such as cyanides in the protocol.

Yet another object of the present invention is to develop a process for easy workup as well as purification of the product.

Still another object of the present invention is to develop a process, which requires economical chemical reagents.

Yet another object of the present invention is to develop a process for the formation of products to be used in flavor, perfumery, pharmaceutical and cosmetic industries.

Yet another object of the present invention is to develop a convenient process for the preparation of anti-cancer compound such as sintenin.

Yet another object of the present invention is to prepare high valued octyl methoxy cinnamate, an important sun-screening agent and UV filter.

SUMMARY OF THE INVENTION

Accordingly, the present invention provides a green process for the direct conversion of cinnamaldehydes or cinnamyl alcohols into various alkyl or aryl substituted cinnamic esters with exclusively E-stereoselectivity. The obtained cinnamic esters, have enormous importance in flavor, perfumery, pharmaceutical and cosmetic industries besides their role as intermediates for synthesis of various biologically active compounds. The method for this transformation is extremely simple and involves reaction of the cinnamaldehydes or cinnamyl alcohols with an oxidizing agent and a catalyst, with suitable alcohol with or without an organic solvent by stirring at room temperature or refluxing or under microwave or ultrasound irradiation for 1 min to 20 hours to get the requisite products. The oxidant for this process is selected from a group consisting of 2,3-dichloro-5,6-dicyano-p-benzoquinone (DDQ) or chloranil or SeO$_2$ and the like. The catalyst is selected from group consisting of homogeneous inorganic or organic catalysts such as hydrochloric acid, sulphuric acid, nitric acid, formic acid, acetic acid, propionic acid, oxalic acid, ionic liquid and the like or heterogeneous catalyst such as AMBERLYST® 15, AMBERLITE® IR 120, AMBERLITE® IR 400, silica gel, alumina (acidic, basic and neutral), celite, kieselguhar and K-10 montmorillonite and the like. The alcohol used for esterification is selected from a group consisting of aliphatic or aromatic alcohols such as methanol, ethanol, propanol, 2-propanol, n-propyl alcohol, butanol, octanol, dodecanol, cinnamyl alcohol, benzyl alcohol, phenyl propanol, phenyl butanol and the like. The process is carried out with or without an organic solvent. Organic solvent, wherever used, is selected from a group consisting toluene, dichlorobenzene, xylene, dichloromethane, diphenyl ether, dioxane, ethylacetate, chloroform and the like. The final products are obtained in stereoselectively trans fashion in high yield varying from 51-98% depending upon the nature of substrate and reagent mixture.

DETAILED DESCRIPTION OF THE INVENTION

Figure 1:
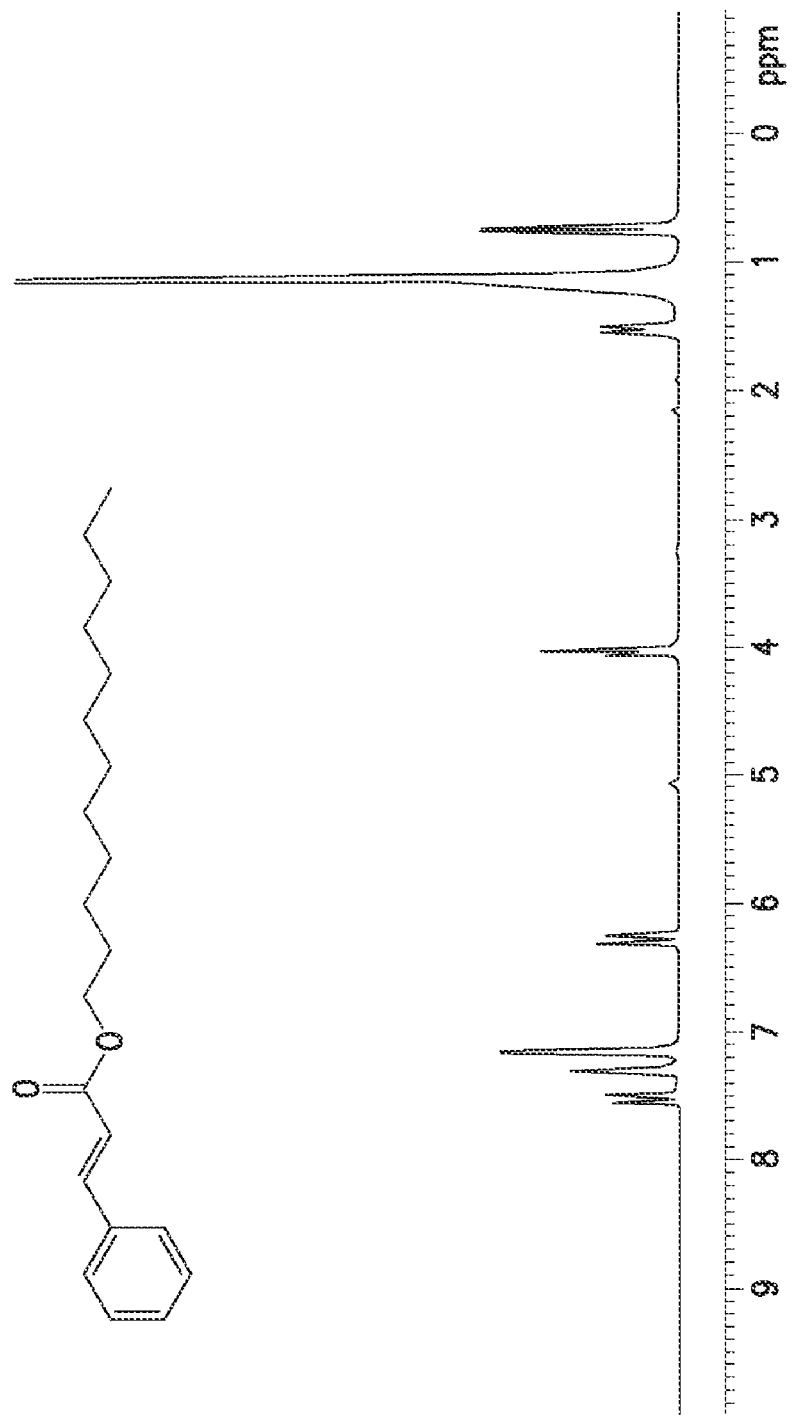
FIG. 1 is $^1$H NMR (300 MHz) spectra of Dodecyl 3-(phenyl)-2-propenoate (in CDCl$_3$).
Figure 2:
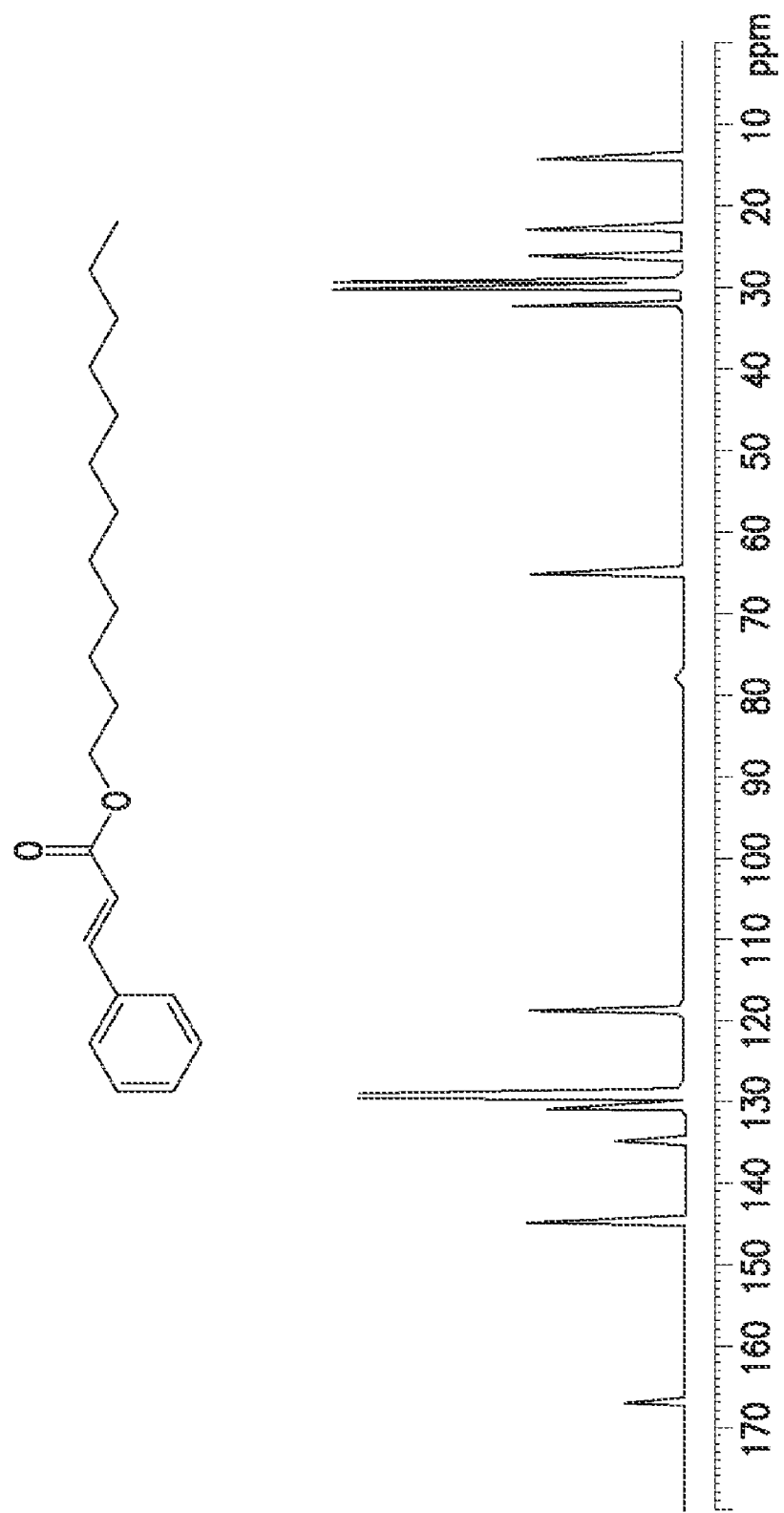
FIG. 2 is $^{13}$C NMR (75.4 MHz) spectra of Dodecyl 3-(phenyl)-2-propenoate (in CDCl$_3$).
Figure 3:
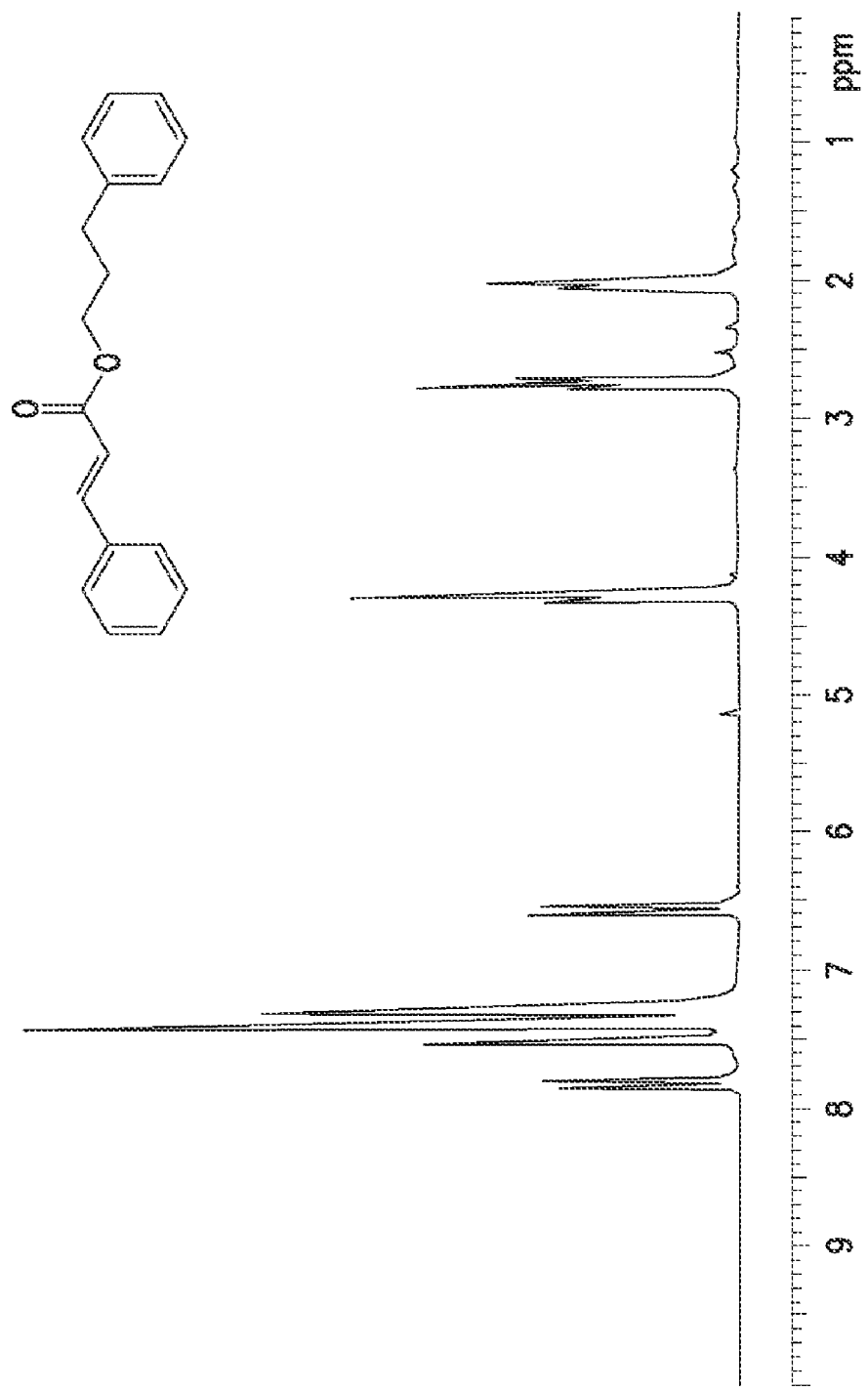
FIG. 3 is $^1$H NMR (300 MHz) spectra of 3-Phenylpropyl 3-(phenyl)-2-propenoate (in CDCl$_3$).
Figure 4:
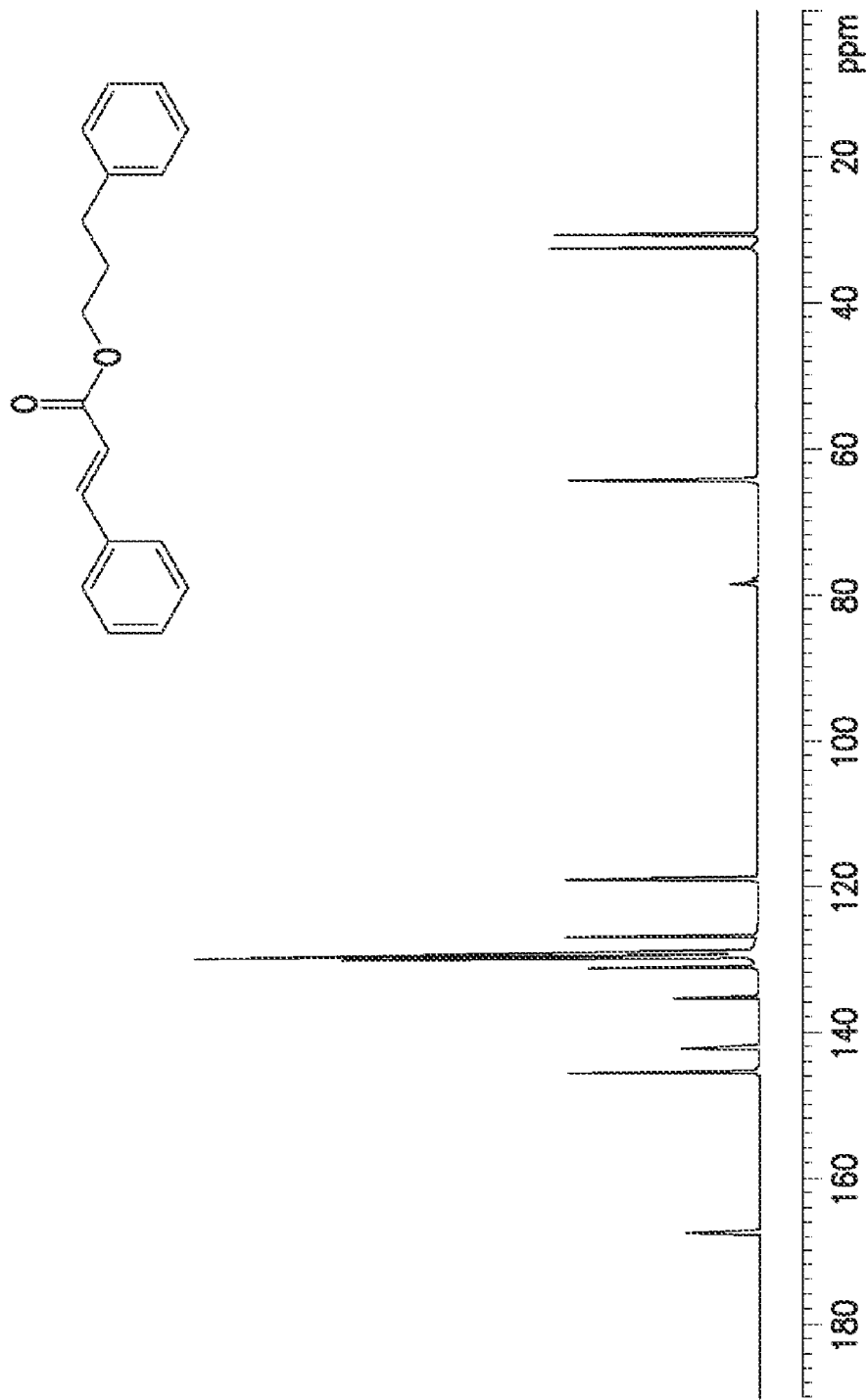
FIG. 4 is $^{13}$C NMR (75.4 MHz) spectra of 3-Phenylpropyl 3-(phenyl)-2-propenoate (in CDCl$_3$).

Accordingly, the present invention provides a single step green process for the Preparation of Substituted Cinnamic Esters with trans-Selectivity of general formula I

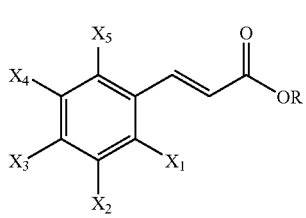

Formula I wherein $X_1$, $X_2$, $X_3$, $X_4$ and $X_5$ are the same or different from each other and each represent a group selected from hydrogen atom, alkoxy group having 1 to 3 carbon atoms, halide group, sulfide group, haloalkyl group having 1 to 3 carbon atoms, amino group, cyano group; and R is selected from a group consisting of alkyl, aryl, arylalkyl or cycloalkyl group having carbon chain from 1 to 20 with or without substitutions at the aromatic ring and the process comprising the steps of;

a) reacting cinnamaldehydes or cinnamyl alcohols of Formula II,

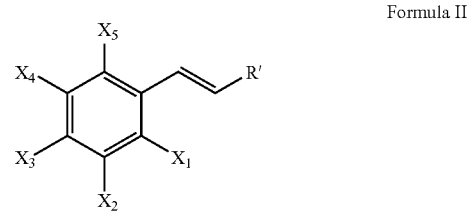

Formula II wherein R' is either CHO or CH$_2$OH; $X_1$, $X_2$, $X_3$, $X_4$ and $X_5$ are the same or different from each other and each represent a group selected from hydrogen atom, alkoxy group having 1 to 3 carbon atoms, halide group, sulfide group, haloalkyl group having 1 to 3 carbon atoms, amino group, cyano group, with an oxidant, a catalyst and an alcohol, optionally along with an organic solvent under stirring at room temperature or refluxing or under microwave irradiation or ultrasound for 1 min-20 hrs, b) filtering the reaction mixture of step (a) and collecting the filtrate, c) filtrate obtained from step (b) is either concentrated or directly passed through a column of solid adsorbent selected from a group consisting of alumina, silica gel, d) eluting the packed column of step (c) with solvents of different polarities to obtain the required product of general formula (I) up to 98% yield.

In another embodiment of the present invention, wherein the developed process is used for the direct oxidation of cinnamaldehydes or cinnamyl alcohols into valuable cinnamic esters of formula I.

In another embodiment of the present invention, wherein the developed process is used for the preparation of esters such as alkyl, aryl, arylalkyl, cyclo alkyl cinnamates and the like.

In another embodiment of the present invention, the substrates used are either cinnamaldehydes or cinnamyl alcohols.

In another embodiment of the present invention, wherein the product formed is stereoselective with exclusively E-selectivity.

In another embodiment of the present invention, the oxidizing agent is selected from group consisting of DDQ, chloranil, selenium dioxide and the like.

In another embodiment of the present invention, the ratio of the substrate and oxidizing agent is ranging from 1:1 to 1:5 preferably 1:2 to 1:3 depending upon substrate used.

In another embodiment of the present invention, wherein the oxidant used for carrying out the reaction is regenerated and reused for a number of times.

In another embodiment of the present invention, the catalyst is selected from a group consisting of homogeneous inorganic or organic catalysts such as hydrochloric acid, sulphuric acid, nitric acid, formic acid, acetic acid, propionic acid, oxalic acid, ionic liquid and the like or heterogeneous catalyst such as AMBERLYST® 15, AMBERLITE® IR 120, AMBERLITE® IR 400, silica gel, alumina (acidic, basic and neutral), celite, kieselguhar and K-10 montmorillonite and the like.

In yet another embodiment of the present invention, the ratio of the catalyst and oxidizing agent is ranging from 1:20 to 1:500.

In another embodiment of the present invention, the alcohol used for the reaction is selected from a group comprising aliphatic or aromatic alcohols such as methanol, ethanol, propanol, 2-propanol, n-propyl alcohol, butanol, octanol, dodecanol, cinnamyl alcohol, benzyl alcohol, phenyl propanol, phenyl butanol and the like.

In yet another embodiment of the present invention, the organic solvent selected from toluene, dichlorobenzene, xylene, dichloromethane, diphenyl ether, dioxane, ethylacetate, chloroform and others.

In another embodiment of the present invention, the process may be carried out without organic solvent depending upon the alcohol used.

In yet another embodiment of the present invention, wherein the process developed is eco-friendly as recyclable reagents, microwave and ultrasound are used for the preparation of product.

In yet another embodiment of the present invention, wherein the heterogeneous catalyst used for carrying out the reaction is recyclable and reused for a number of times preferably for 5 to 15 times, without any significant loss in the activity.

In yet another embodiment of the present invention, wherein the method is found equally workable at room temperature, refluxing temperature, in monomode and multimode microwave and ultrasound.

In another embodiment of the present invention, the reaction is carried out by stirring the reaction mixture at room temperature for 3-20 hrs preferably 5 hrs to 9 hours.

In another embodiment of the present invention, the reaction is carried out by refluxing the reaction mixture for 1-10 hrs preferably 1 hrs to 6 hours.

In yet another embodiment of the present invention, the reaction is carried out in a domestic microwave oven operated at 700 W-1500 W power level for 10 min-80 min preferably 1 min to 45 min.

In yet another embodiment of the present invention, the reaction is successfully performed in a monomode microwave organic synthesizer operated at 50 W-300 W power level with 70-250° C. for 1 min-50 min preferably 1 min-30 min.

In another embodiment of the present invention, the microwave irradiation frequency used is in the range of 900 to 3000 MHz more preferably 2450 to 2455 MHz.

In another embodiment of the present invention, wherein the temperature attained in case of the microwave is ranging from 100-250° C. preferably 110-170° C.

In yet another embodiment of the present invention, wherein the reaction is carried out under ultrasound irradiation.

In yet another embodiment of the present invention, wherein the ultrasonicator is operated at 50-90% duty for 1-6 hours, at 20 KHz-40 KHz frequency.

In yet another embodiment of the present invention, combination of reagents used is non-hazardous.

In yet another embodiment of the present invention, a process where the reaction produces yield of the products up to 98% yield depending upon the substrate.

In yet another embodiment of the present invention, wherein the process is free from side products.

In yet another embodiment of the present invention, combination of reagents used is economical.

The present invention relates to a single step Green Process for the Preparation of Substituted Cinnamic Esters with trans-Selectivity in which commercially important cinnamic esters such as octyl methoxy cinnamate (a sunscreening agent) (G. Yener, T. Incegul, N. Yener, *Int. J. Pharm.*, 2005, 258, 203), sintenin (an anti-cancer agent) (L. H. Hu, H. B. Zou, J. X. Gong, H. B. Li, L. X. Yang, W Cheng, C. X. Zhou, H. Bai, F. Gueritte, Y. Zhau, *J. Nat. Prod.*, 2005, 68, 342) and methyl cinnamate (a flavoring agent) (A. Steffen, *Perfume and Flavor Chemicals (Aroma Chemicals)*, Vol. I & II. Allured Publishing Corporation: IL, USA, 1994)) are obtained. The reaction proceeds through direct conversion of either cinnamaldehydes or cinnamyl alcohols into cinnamic esters in the presence of an oxidant, a catalyst and an alcohol, with or without an organic solvent in either conventional conditions or microwave or ultrasound irradiations. The oxidant for this process is selected from a group consisting of 2,3-dichloro-5,6-dicyano-p-benzoquinone (DDQ) or chloranil or $SeO_2$ and the like. The alcohol used for esterification is selected from a group consisting of aliphatic or aromatic alcohols such as methanol, ethanol, propanol, 2-propanol, n-propyl alcohol, butanol, octanol, dodecanol, cinnamyl alcohol, benzyl alcohol, phenyl propanol, phenyl butanol and the like. The catalyst is selected from group consisting of homogeneous inorganic or organic catalysts such as hydrochloric acid, sulphuric acid, nitric acid, formic acid, acetic acid, propionic acid, oxalic acid, ionic liquid and the like or heterogeneous catalyst such as AMBERLYST® 15, AMBERLITE® IR 120, AMBERLITE® IR 400, silica gel, alumina (acidic, basic and neutral), celite, kieselguhar and K-10 montmorillonite and the like. The process is carried out with or without an organic solvent. Organic solvent, wherever used, is selected from a group consisting toluene, dichlorobenzene, xylene, dichloromethane, diphenyl ether, dioxane, ethylacetate, chloroform and the like. The reaction time varies from 1 min to 20 hrs depending upon the nature of substrate used and the mode of reaction as stirring at room temperature or refluxing, use of monomode or multimode microwave or ultrasound. Yield varies from 51-98% depending upon the substrate, oxidant, alcohol, catalyst and solvent used.

We have already seen the successful effect of oxidation by DDQ on phenyl propanoids ((a) B. P. Joshi, A. Sharma, A. K. Sinha, *Tetrahedron*, 2005, 61, 3075; (b) A. K. Sinha, B. P. Joshi, R. Dogra, U.S. Pat. No. 6,566,557, 2003; (c) A. K. Sinha, B. P. Joshi, R. Dogra, U.S. Pat. No. 6,590,127, 2003) and decided to extend it our case due to benefits such as mild oxidation, recycling ability of the spent catalyst and good yields. It was also decided to initially activate DDQ by protonation from an acid. Hence, we decided to use a mild heterogeneous catalyst in the form of resin for this reaction. Initially, cinnamaldehyde was refluxed with the oxidizing agent and a homogeneous or heterogeneous catalyst, in the presence of methanol, which provided 82% yield of the product methyl cinnamate. To further increase the yield of the product various alterations in the reaction were made. After a lot of experimentation, it was found that oxidizing agent and the homogeneous or heterogeneous catalyst, with a combination of methanol and an organic solvent over a dean stark for 4-10 hrs provided optimum yield of the product up to 95-98%. After success of formation of methyl cinnamate, methyl esters were prepared with various other substituted cinnamaldehydes and the corresponding methyl esters are prepared in very good yields within 4-8 hr of refluxing of MeOH, oxidizing agent, homogeneous or heterogeneous catalyst, organic solvent and the respective cinnamaldehydes.

Moreover, various homogeneous or heterogeneous catalysts were tested and reaction occurred in all of them, though the yield varied as the examples in the next section illustrates them.

Similarly, impact of the alcohols on the esterification reaction was also examined, and as the example section would suggest, the structure of the alcohol has some influence on the end yield of the product.

The above method was also tested by stirring at room temperature. The reaction was also tested under microwave as well as ultrasound and the method was found equally effective in all the three.

The oxidizing agent in our protocol may be regenerated by the reported methods. The heterogeneous catalyst may be retrieved back by mere filtration of the product and was found to be effective for at least fifteen cycles of reuse.

In conclusion, we have invented a resin-catalyzed oxidation of substituted cinnamaldehydes or cinnamyl alcohols with DDQ in a clean and practical method for the synthesis of various bioactive cinnamates in high yield without either using strong acids or hazardous oxidizing agents. Moreover, the oxidant as well as the catalyst are recyclable and thus effectively handle waste management making the process more economical.

The following examples are given by way of illustration of the present invention and should not be construed to limit the scope of the present invention.

EXAMPLE 1

Method for the Preparation of Methyl Cinnamate from Cinnamaldehyde Using Conventional Method (At Room Temperature)

A homogeneous mixture containing cinnamaldehyde (7.5 mmol), DDQ (11.3 mmol), MeOH (15 mL) is taken in a round bottom flask and catalytic amount of AMBERLYST® 15 (0.1 g) is added to it. The mixture is stirred for 20 hrs at room temperature. After completion of the reaction (observed by TLC and GC analysis), the reaction mixture is filtered and washed with MeOH (5 ml×2). Concentrate the filtrate under reduced pressure and the crude product thus obtained is loaded on a neutral alumina column and eluted with diethyl ether. Methyl cinnamate (from formula I where $X_1$=H, $X_2$=H, $X_3$=H, $X_4$=H, $X_5$=H, R=$CH_3$) is isolated in 98% yield. $^1$H-NMR ($CDCl_3$, 300 MHz) δ7.56 (1H, d, J=16.55 Hz), 7.34 (2H, m), 7.21 (3H, m), 6.31 (1H, d, J=16.55 Hz), 3.64 (3H, s); $^{13}$C-NMR ($CDCl_3$, 75.4 MHz) δ167.2, 144.7, 134.3, 130.2, 128.8, 128.0, 117.8, 51.5.

EXAMPLE 2

Method for the Preparation of Methyl Cinnamate from Cinnamyl Alcohol Using Conventional Method (At Room Temperature)

A homogeneous mixture containing cinnamyl alcohol (7.5 mmol), DDQ (22.5 mmol), MeOH (20 mL) is taken in a round bottom flask and catalytic amount of AMBERLYST® 15 (0.1 g) is added to it. The mixture is stirred for 20 hrs at room temperature. After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. Methyl cinnamate is isolated in 86% yield whose NMR values are found matching with reported values as in example 1.

EXAMPLE 3

Method for the Preparation of Methyl Alpha Methyl Cinnamate from Cinnamaldehyde Using Conventional Method (At Room Temperature)

A homogeneous mixture containing alpha methyl cinnamaldehyde (7.5 mmol), DDQ (11.3 mmol), MeOH (15 mL) is taken in a round bottom flask and catalytic amount of acidic alumina 15 (0.1 g) is added to it. The mixture is stirred for 20 hrs at room temperature. After completion of the reaction (observed by TLC and GC analysis), the reaction mixture is filtered and washed with MeOH (5 ml×2). Concentrate the filtrate under reduced pressure and the crude product thus obtained is loaded on a neutral alumina column and eluted with diethyl ether. Methyl alpha methyl cinnamate (from formula I where $X_1$=H, $X_2$=H, $X_3$=H, $X_4$=H, $X_5$=H, R=$CH_3$) is isolated in 55% yield. $^1$H-NMR ($CDCl_3$, 300 MHz) δ7.61 (1H, s), 7.23 (5H, m), 3.69 (3H, s), 2.05 (3H, s); $^{13}$C-NMR ($CDCl_3$, 75.4 MHz) δ168.9, 138.9, 135.8, 129.6, 128.3, 51.3, 14.0.

EXAMPLE 4

Method for the Preparation of Isopropyl Cinnamate from Cinnamaldehyde Using Conventional Method (At Room Temperature)

A homogeneous mixture containing cinnamaldehyde (7.5 mmol), Chloronil (22.5 mmol), isopropanol (10 mL) is taken in a round bottom flask and catalytic amount of silica gel (0.1 g) is added to it. The mixture is stirred for 20 hrs at room temperature. After completion of the reaction (observed by TLC and by GC analysis), the reaction mixture is filtered and washed with ethylacetate (5 ml×2). Concentrate the filtrate under reduced pressure and the crude product thus obtained is loaded on a neutral alumina column and eluted with diethyl ether. Isopropyl cinnamate (from formula I where $X_1$=H, $X_2$=H, $X_3$=H, $X_4$=H, $X_5$=H, R=$C_3H_8$) is isolated in 49% yield. $^1$H-NMR ($CDCl_3$, 300 MHz) δ7.59 (1H, d, J=16.55 Hz), 7.41 (2H, m), 7.27 (3H, m), 6.34 (1H, d, J=16.55 Hz), 5.07 (1H, m), 1.18 (6H, d); $^{13}$C-NMR ($CDCl_3$, 75.4 MHz) δ166.4, 144.3, 134.5, 130.1, 128.6, 128.0, 118.8, 67.7, 21.9.

EXAMPLE 5

Method for the Preparation of 3-Phenylpropyl Cinnamate from Cinnamaldehyde Using Conventional Method (At Room Temperature)

A homogeneous mixture containing cinnamaldehyde (7.5 mmol), DDQ (22.5 mmol), 3-phenylpropanol (10 mL) and toluene (10 mL) is taken in a round bottom flask and catalytic amount of Montmorillonite K10 15 (0.1 g) is added to it. The mixture is stirred for 20 hrs at room temperature. After completion of the reaction (observed by TLC and by GC analysis), the reaction mixture is filtered and washed with ethylacetate (5 ml×2). Concentrate the filtrate under reduced pressure and the crude product thus obtained is loaded on a neutral alumina column and eluted with diethyl ether. 3-Phenylpropyl cinnamate (from formula I where $X_1$=H, $X_2$=H, $X_3$=H, $X_4$=H, $X_5$=H, R=$C_9H_{11}$) is isolated in 84% yield.

¹H-NMR (CDCl₃, 300 MHz) δ7.74 (1H, d), 7.43 (2H, m), 7.28 (5H, m), 7.19 (3H, m), 6.48 (2H, d), 4.22 (2H, t), 2.69 (2H, t), 1.98 (2H, t); ¹³C-NMR (CDCl₃, 75.4 MHz) δ166.7, 144.7, 141.4, 134.6, 130.6, 129.2, 128.6, 127.4, 126.5, 118.4, 63.9, 32.3, 30.5.

EXAMPLE 6

Method for the Preparation of Methyl 4-Methoxycinnamate from 4-Methoxycinnamaldehyde Using Conventional Method (Refluxing Under Dean Stark Apparatus)

A homogeneous mixture containing 4-methoxycinnamaldehyde (7.5 mmol), DDQ (11.3 mmol), MeOH (15 mL) and toluene (10 mL) is taken in a round bottom flask and catalytic amount of AMBERLITE® IR 400 (0.1 g) is added to it. The mixture is refluxed for 6 hrs under Dean Stark apparatus. After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. Methyl 4-methoxycinnamate (from formula I where $X_1$=H, $X_2$=H, $X_3$=OCH₃, $X_4$=H, $X_5$=H, R=CH₃) is isolated in 91% yield. ¹H-NMR (CDCl₃, 300 MHz) δ7.56 (1H, d, J=16.55 Hz), 7.37 (2H, d), 6.80 (2H, d), 6.22 (1H, d, J=16.55 Hz), 3.73 (3H, s), 3.70 (3H, s); ¹³C-NMR (CDCl₃, 75.4 MHz) δ167.7, 161.4, 144.5, 129.7, 127.1, 115.2, 114.3, 55.3, 51.5.

EXAMPLE 7

Method for the Preparation of Methyl 2,4,5-Trimethoxycinnamate from 2,4,5-Methoxycinnamaldehyde Using Conventional Method (Refluxing Under Dean Stark Apparatus)

A homogeneous mixture containing 2,4,5-trimethoxycinnamaldehyde (7.5 mmol), DDQ (11.3 mmol), MeOH (15 mL) and toluene (10 mL) is taken in a round bottom flask and catalytic amount of AMBERLITE® IR 120 (0.1 g) is added to it. The mixture is refluxed for 6 hrs under Dean Stark apparatus. After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. Methyl 2,4,5-trimethoxycinnamate (from formula I where $X_1$=OCH₃, $X_2$=H, $X_3$=OCH₃, $X_4$=OCH₃, $X_5$=H, R=CH₃) is isolated in 84% yield. ¹H-NMR (CDCl₃, 300 MHz) δ7.91 (1H, d, J=16.10 Hz), 7.01 (1H, s), 6.50 (1H, s), 6.37 (1H, d, J=16.10 Hz), 3.93 (3H, s), 3.88 (3H, s), 3.87 (3H, s), 3.80 (3H, s); ¹³C-NMR (CDCl₃, 75.4 MHz) δ168.2, 153.9, 151.9, 143.4, 139.7, 116.6, 115.4, 112.6, 96.9, 56.5, 56.4, 56.1, 51.5.

EXAMPLE 8

Method for the Preparation of Methyl Cinnamate From Cinnamaldehyde Using Conventional Method (Refluxing Under Dean Stark Apparatus)

A homogeneous mixture containing cinnamaldehyde (7.5 mmol), DDQ (11.3 mmol), MeOH (15 mL) and toluene (10 mL) is taken in a round bottom flask and catalytic amount of acetic acid (5 drops) is added to it. The mixture is refluxed for 6 hrs under Dean Stark apparatus. After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. Methyl cinnamate is isolated in 98% yield whose NMR values are found matching with reported values as in example 1.

EXAMPLE 9

Method for the Preparation of Methyl Cinnamate from Cinnamaldehyde Using Conventional Method (Refluxing Under Dean Stark Apparatus)

A homogeneous mixture containing cinnamaldehyde (7.5 mmol), DDQ (11.3 mmol), MeOH (15 mL) and toluene (10 mL) is taken in a round bottom flask and catalytic amount of neutral alumina (0.1 g) is added to it. The mixture is refluxed for 6 hrs under Dean Stark apparatus. After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. Methyl cinnamate is isolated in 96% yield whose NMR values are found matching with reported values as in example 1.

EXAMPLE 10

Method for the Preparation of Ethyl Cinnamate from Cinnamaldehyde Using Conventional Method (Refluxing Under Dean Stark Apparatus)

A homogeneous mixture containing cinnamaldehyde (7.5 mmol), DDQ (11.3 mmol), EtOH (15 mL) and toluene (10 mL) is taken in a round bottom flask and catalytic amount of AMBERLYST® 15 (0.1 g) is added to it. The mixture is refluxed for 6 hrs under Dean Stark apparatus. After completion of the reaction (observed by TLC and by GC analysis), the reaction mixture is filtered and washed with EtOH (10 ml×2). Concentrate the filtrate under reduced pressure and the crude product thus obtained is loaded on a neutral alumina column and eluted with diethyl ether. Ethyl cinnamate (from formula I where $X_1$=H, $X_2$=H, $X_3$=H, $X_4$=H, $X_5$=H, R=C₂H₅) is isolated in 94% yield. ¹H-NMR (CDCl₃, 300 MHz) δ7.72 (1H, d, J=16.19 Hz), 7.43 (5H, m), 6.47 (1H, d, J=16.19 Hz), 4.28 (2H, q, J=7.09 Hz), 1.34 (3H, t, J=7.09 Hz); ¹³C-NMR (CDCl₃, 75.4 MHz) δ166.9, 144.5, 130.1, 128.8, 128.5, 127.9, 118.2, 60.4, 14.2.

EXAMPLE 11

Method for the Preparation of Butyl Cinnamate from Cinnamaldehyde Using Conventional Method (Refluxing Under Dean Stark Apparatus)

A homogeneous mixture containing cinnamaldehyde (7.5 mmol), DDQ (11.3 mmol), BuOH (10 mL) and toluene (15 mL) is taken in a round bottom flask and catalytic amount of AMBERLYST® 15 (0.1 g) is added to it. The mixture is refluxed for 6 hrs under Dean Stark apparatus. After completion of the reaction (observed by TLC and by GC analysis), the reaction mixture is filtered and washed with ethylacetate (5 ml×2). Concentrate the filtrate under reduced pressure and the crude product thus obtained is loaded on a neutral alumina column and eluted with diethyl ether. Butyl cinnamate (from formula I where $X_1$=H, $X_2$=H, $X_3$=H, $X_4$=H, $X_5$=H, R=$C_4H_9$) is isolated in 94% yield. $^1$H-NMR (CDCl$_3$, 300 MHz) δ7.48 (1H, d), 7.25 (2H, m), 7.11 (3H, m), 6.23 (1H, m), 3.98 (2H, t), 1.45 (2H, m), 1.19 (2H, m), 0.74 (3H, t); $^{13}$C-NMR (CDCl$_3$, 75.4 MHz) δ166.5, 144.2, 134.4, 129.9, 127.9, 118.2, 64.0, 30.7, 19.1, 13.6.

EXAMPLE 12

Method for the Preparation of Octyl Cinnamate from Cinnamaldehyde Using Conventional Method (Refluxing Under Dean Stark Apparatus)

A homogeneous mixture containing cinnamaldehyde (7.5 mmol), DDQ (11.3 mmol), octanol (15 mL) and dioxane (10 mL) is taken in a round bottom flask and catalytic amount of AMBERLYST® 15 (0.1 g) is added to it. The mixture is refluxed for 6 hrs under Dean Stark apparatus. After completion of the reaction (observed by TLC and by GC analysis), the reaction mixture is filtered and washed with ethylacetate (5 ml×2). Concentrate the filtrate under reduced pressure and the crude product thus obtained is loaded on a neutral alumina column and eluted with diethyl ether. Octyl cinnamate (from formula I where $X_1$=H, $X_2$=H, $X_3$=H, $X_4$=H, $X_5$=H, R=$C_8H_{17}$) is isolated in 86% yield. $^1$H-NMR (CDCl$_3$, 300 MHz) δ7.51 (1H, d), 7.46 (2H, m), 7.26 (3H, m), 6.24 (1H, d), 3.93 (2H, m), 1.43 (2H, m), 1.16 (8H, m), 0.73 (5H, m); $^{13}$C-NMR (CDCl$_3$, 75.4 MHz) δ166.5, 144.2, 134.4, 129.9, 128.6, 127.9, 118.2, 66.5, 38.8, 30.4, 28.9, 23.8, 22.9, 13.9, 10.9.

EXAMPLE 13

Method for the Preparation of Dodecyl Cinnamate from Cinnamaldehyde Using Conventional Method (Refluxing Under Dean Stark Apparatus)

A homogeneous mixture containing cinnamaldehyde (7.5 mmol), SeO$_2$ (11.3 mmol), dodecanol (5 mL) and toluene (10 mL) is taken in a round bottom flask and catalytic amount of neutral alumina (0.1 g) is added to it. The mixture is refluxed for 6 hrs under Dean Stark apparatus. After completion of the reaction (observed by TLC and by GC analysis), the reaction mixture is filtered and washed with ethylacetate (5 ml×2). Concentrate the filtrate under reduced pressure and the crude product thus obtained is loaded on a neutral alumina column and eluted with diethyl ether. Dodecylcinnamate (from formula I where $X_1$=H, $X_2$=H, $X_3$=H, $X_4$=H, $X_5$=H, R=$C_{12}H_{25}$) is isolated in 87% yield. $^1$H-NMR (CDCl$_3$, 300 MHz) δ7.51 (1H, d), 7.28 (2H, m), 7.14 (3H, m), 6.26 (1H, d), 4.02 (2H, t), 1.50 (2H, t), 1.11 (18H, m), 0.73 (3H, d); $^{13}$C-NMR (CDCl$_3$, 75.4 MHz) δ166.4, 144.2, 134.4, 129.6, 128.6, 127.9, 118.2, 64.3, 31.9, 29.7, 29.6, 29.4, 28.7, 26.0, 22.7, 14.0.

EXAMPLE 14

Method for the Preparation of 2-Methoxyethyl Cinnamate from Cinnamaldehyde Using Conventional Method (Refluxing Under Dean Stark Apparatus)

A homogeneous mixture containing cinnamaldehyde (7.5 mmol), DDQ (11.3 mmol), 2-methoxyethanol (25 mL) and toluene (10 mL) is taken in a round bottom flask and catalytic amount of basic alumina (0.1 g) is added to it. The mixture is refluxed for 6 hrs under Dean Stark apparatus. After completion of the reaction (observed by TLC and by GC analysis), the reaction mixture is filtered and washed with ethylacetate (5 ml×2). Concentrate the filtrate under reduced pressure and the crude product thus obtained is loaded on a neutral alumina column and eluted with diethyl ether. 2-Methoxyethyl cinnamate (from formula I where $X_1$=H, $X_2$=H, $X_3$=H, $X_4$=H, $X_5$=H, R=$C_3H_7O$) is isolated in 93% yield. $^1$H-NMR (CDCl$_3$, 300 MHz) δ7.51 (1H, d, J=16.55 Hz), 7.28 (2H, m), 7.15 (3H, m), 6.28 (1H, d, J=16.55 Hz), 4.16 (2H, t), 3.44 (2H, t), 3.18 (3H, s); $^{13}$C-NMR (CDCl$_3$, 75.4 MHz) δ166.6, 144.8, 134.3, 130.2, 128.8, 117.8, 70.4, 63.4, 58.7.

EXAMPLE 15

Method for the Preparation of 2-Hydroxyethyl Cinnamate from Cinnamaldehyde Using Conventional Method (Refluxing Under Dean Stark Apparatus)

A homogeneous mixture containing cinnamaldehyde (7.5 mmol), DDQ (11.3 mmol), ethylene glycol (10 mL) is taken in a round bottom flask and catalytic amount of AMBERLYST® 15 (0.1 g) is added to it. The mixture is refluxed for 6 hrs under Dean Stark apparatus. After completion of the reaction (observed by TLC and by GC analysis), the reaction mixture is filtered and washed with ethylacetate (5 ml×2). Concentrate the filtrate under reduced pressure and the crude product thus obtained is loaded on a neutral alumina column and eluted with diethyl ether. 2-Hydroxyethyl cinnamate (from formula I where $X_1$=H, $X_2$=H, $X_3$=H, $X_4$=H, $X_5$=H, R=$C_2H_5O$) is isolated in 88% yield. $^1$H-NMR (CDCl$_3$, 300 MHz) δ7.65 (1H, d, J=16.55 Hz), 7.42 (2H, m), 7.29 (3H, m), 6.38 (1H, d, J=16.55 Hz), 4.37 (2H, t), 3.66 (2H, t); $^{13}$C-NMR (CDCl$_3$, 75.4 MHz) δ166.4, 145.6, 134.2, 130.5, 128.9, 128.2, 117.3, 64.1, 41.8.

EXAMPLE 16

Method for the Preparation of Methyl Cinnamate from Cinnamaldehyde Using Multimode Microwave A homogeneous mixture containing cinnamaldehyde (7.5 mmol), DDQ (11.3 mmol), MeOH (10 mL) is taken in an Erlenmeyer flask (150 ml) and catalytic amount of AMBERLYST® 15 (0.1 g) is added to it. The mixture is irradiated for 10 min under multimode microwave at 900 W power level. After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. The yield of the methyl cinnamate is 95% whose NMR values are found matching with reported values as in example 1.

EXAMPLE 17

Method for the Preparation of Methyl Cinnamate from Cinnamaldehyde Using Monomode Microwave A homogeneous mixture containing cinnamaldehyde (7.5 mmol), DDQ (11.3 mmol), MeOH (10 mL) is taken in a 100 ml round bottom flask and catalytic amount of AMBERLYST® 15 (0.1 g) is added to it. The mixture is irradiated for 10 min under monomode microwave at 100 W and 125° C. After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. The yield of the methyl cinnamate is 98% whose NMR values are found matching with reported values as in example 1.

EXAMPLE 18

Method for the Preparation of Methyl Cinnamate from Cinnamaldehyde Using Ultrasound Irradiation A homogeneous mixture containing cinnamaldehyde (7.5 mmol), DDQ (11.3 mmol), MeOH (15 mL) is taken in a 100 ml beaker and catalytic amount of AMBERLYST® 15 (0.1 g) is added to it. The mixture is irradiated for 6 hr under ultrasonicator for sonication (pulse length 9 sec, pause after 20 min, duty 80%). After completion of the reaction (observed by TLC and by GC analysis), the reaction mixture is filtered and washed with MeOH (5 ml×2). Concentrate the filtrate under reduced pressure and the crude product thus obtained is loaded on a neutral alumina column and eluted with diethyl ether. The yield of the methyl cinnamate is 92% whose NMR values are found matching with reported values as in example 1.

THE MAIN ADVANTAGES OF THE PRESENT INVENTION

The main advantage of the present invention is "A Green Process for the Preparation of Substituted Cinnamic Esters with trans-Selectivity" in which high valued food flavorings, cosmetic and most importantly, pharmaceutically important alkyl or aryl cinnamates are obtained from cinnamaldehydes or cinnamyl alcohols.
1. A process for direct conversion of cinnamaldehydes or cinnamyl alcohols into cinnamic esters in one pot.
2. A process for the synthesis of cinnamic esters in excellent yield ranging from 51-98%.
3. A process to employ ecofriendly and non-hazardous reagents for the preparation of unsaturated carbonyl compounds.
4. A process to prepare cinnamic esters in a few hours without any side products.
5. A process which is equally applicable in monomode multimode microwave and ultrasound irradiation.
6. A process which is equally workable in both monomode and multimode microwave instruments.
7. A process in which the catalyst is economical and environment friendly.
8. A process which utilizes less or non-hazardous chemicals.
9. An environment-friendly green process is developed wherein the oxidizing agent and the heterogeneous catalyst used is regenerated and reusable.
10. An industrially viable process towards formation of high valued alkyl/aryl cinnamates wherein the catalyst used is recyclable and there is no loss in the activity even after many cycles of use.
11. An industrially viable process, which is ecofriendly by virtue of employment of non-hazardous reagents and short reaction time.
12. An industrially viable process in which products formed can be used in flavor, perfumery, pharmaceutical and cosmetic industries (as sunscreen).

We claim:
1. A single pot process for the preparation of substituted cinnamic esters with trans-selectivity of Formula I, excluding the toxic and hazardous cyanides as an oxidizing agent:

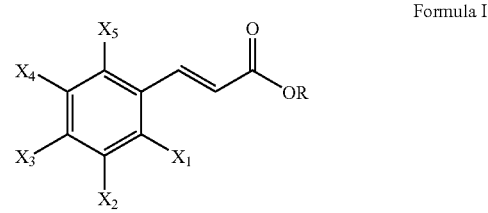

Formula I wherein:
each of $X_1$, $X_2$, $X_3$, $X_4$ and $X_5$ is independently selected from the group consisting of hydrogen atom, an alkoxy group having 1 to 3 carbon atoms, a halide, a sulfide group, a haloalkyl group having 1 to 3 carbon atoms, an amino group, and cyano group; and
R is selected from the group consisting of an alkyl, an aryl, an arylalkyl and an cycloalkyl group having carbon chain from 1 to 20 with or without substitutions at the aromatic ring, the process comprising the steps of:
a) reacting cinnamaldehydes or cinnamyl alcohols of Formula II,

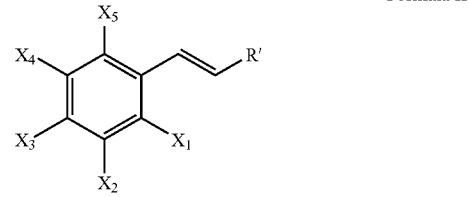

Formula II wherein:
R' is selected from CHO and $CH_2OH$; and
each of $X_1$, $X_2$, $X_3$, $X_4$ and $X_5$ is independently selected from the group consisting of hydrogen atom, an alkoxy group having 1 to 3 carbon atoms, a halide, a sulfide group, a haloalkyl group having 1 to 3 carbon atoms, an amino group, and cyano group,
with an oxidizing agent, a catalyst, and an alcohol, optionally in the presence of an organic solvent, while stirring at room temperature, or refluxing, or under microwave irradiation or ultrasound for a period of time between about 1 minute and about 20 hours, to obtain substituted cinnamic esters of Formula I with trans-selectivity with a yield up to 98% in a single step;
b) filtering the reaction mixture obtained in step (a) and collecting the filtrate;
c) concentrating the filtrate obtained in step (b) or directly passing the same through a column of solid adsorbent selected from the group consisting of alumina and silica gel; and
d) eluting the packed column of step (c) with solvents of different polarities, to obtain the substituted cinnamic esters of Formula I with trans-selectivity free from side products.
2. The process of claim 1, wherein the obtained substituted cinnamic ester of Formula I is stereoselective with exclusively E-selectivity.

3. The process of claim 1, wherein the compounds obtained by the process comprise methyl cinnamate, 2-hydroxyethyl cinnamate, 2-methoxyethyl cinnamate, dodecyl cinnamate, octyl cinnamate, butyl cinnamate, ethyl cinnamate, 3-phenyl-propylcinnamate, methyl 2,4,5-trimethoxycinnamate, methyl 4-methoxycinnamate, methyl alpha methyl cinnamate, or isopropyl cinnamate.

4. The process of claim 1, wherein the oxidizing agent is selected from the group consisting of 2,3-dichloro-5,6-dicyano-p-benzoquinone, chloranil, and selenium dioxide.

5. The process of claim 1, wherein the ratio of the substrate and the oxidizing agent is between about 1:1 and about 1:5.

6. The process of claim 1, wherein the oxidizing agent is regenerated and reused for a plurality of times.

7. The process of claim 1, wherein the catalyst comprises a homogeneous inorganic catalyst, a homogeneous organic catalyst, an ionic liquid catalyst, or a heterogeneous catalyst.

8. The process of claim 1, wherein the ratio of the catalyst and the oxidizing agent is between about 1:20 and about 1:500.

9. The process of claim 1, wherein the alcohol comprises an aliphatic alcohol or an aromatic alcohol.

10. The process of claim 1, wherein the organic solvent is selected from the group consisting of toluene, dichlorobenzene, xylene, dichloromethane, diphenyl ether, dioxane, ethylacetate, and chloroform.

11. The process of claim 1, wherein the process is carried out in the absence of the organic solvent.

12. The process of claim 1, wherein the process utilizes recyclable reagents, microwave and ultrasound for the preparation of product.

13. The process of claim 1, wherein the catalyst is heterogeneous, is recyclable and is reused for a plurality of times without any substantial loss in the activity.

14. The process of claim 1, wherein the reaction is carried out by stirring the reaction mixture at room temperature for a period of time between about 3 hours and about 20 hours.

15. The process of claim 1, wherein the reaction is carried out by refluxing the reaction mixture for a period of time between about 1 hour and about 10 hours.

16. The process of claim 1, wherein the reaction is carried out in a domestic microwave oven operated at the 700 W-1500 W power level for a period of time between about 1 and about 80 minutes.

17. The process of claim 1, wherein the reaction is carried out in a monomode microwave organic synthesizer operated at the 50 W-300 W power level with 70-250° C. for a period of time between about 1 minute and about 50 minutes.

18. The process of claim 1, wherein the microwave irradiation frequency used is in the range of between about 900 MHz and about 3000 MHz.

19. The process of claim 1, wherein the temperature attained in case of the microwave is ranging from between about 100° C. and about 250° C.

20. The process of claim 1, wherein the reaction is carried out under ultrasound irradiation.

21. The process of claim 1, wherein the reaction is carried out under ultrasound irradiation from an ultrasonicator operated at between about 50% and about 90% duty for a period of time between about 1 hour and about 6 hours, at a frequency ranging between about 20 KHz and about 40 KHz.

22. The process of claim 1, wherein the combination of reagents used is non-hazardous.

23. The process of claim 1, wherein the process is substantially free from side products.

24. The process of claim 1, wherein the combination of reagents used is economical.

25. The process of claim 5, wherein the ratio of the substrate and oxidizing agent is between about 1:2 and about 1:3.

26. The process of claim 7, wherein the catalyst is selected from the group consisting of hydrochloric acid, sulphuric acid, nitric acid, formic acid, acetic acid, propionic acid, oxalic acid, AMBERLYST® 15, AMBERLITE® IR 120, AMBERLITE® IR 400, silica gel, alumina (acidic, basic and neutral), celite, kieselguhar and K-10 montmorillonite.

27. The process of claim 9, wherein the alcohol is selected from the group consisting of methanol, ethanol, propanol, 2-propanol, n-propyl alcohol, butanol, octanol, dodecanol, cinnamyl alcohol, benzyl alcohol, phenyl propanol, and phenyl butanol.

28. The process of claim 13, wherein the heterogeneous catalyst is reused between 5 and 15 times.

29. The process of claim 14, wherein the reaction is carried out for a period of time between about 5 hours and about 9 hours.

30. The process of claim 15, wherein the reaction is carried out for a period of time between about 1 hour and about 6 hours.

31. The process of claim 16, wherein the reaction is carried out for a period of time between about 1 minute and about 45 minutes.

32. The process of claim 17, wherein the reaction is carried out for a period of time between about 1 minute and about 30 minutes.

33. The process of claim 18, wherein the microwave irradiation frequency is in the range of between about 2450 MHz and about 2455 MHz.

34. The process of claim 19, wherein the temperature is ranging between about 110° C. and about 170° C.

* * * * *